United States Patent [19]

Gladfelter et al.

[11] Patent Number: 4,535,148

[45] Date of Patent: Aug. 13, 1985

[54] POLYGLYCIDYL ETHERS OF TRICYCLODECANE AND CURED EPOXY RESINS THEREFROM

[75] Inventors: Elizabeth J. Gladfelter, St. Paul; Edgar R. Rogier, Minnetonka; Edward D. DiDomenico, Anoka, all of Minn.

[73] Assignee: Henkel Corporation, Minneapolis, Minn.

[21] Appl. No.: 636,645

[22] Filed: Aug. 1, 1984

[51] Int. Cl.³ .................... C08G 59/34; C08G 59/32
[52] U.S. Cl. ................................ 528/365; 528/406; 528/407; 549/523; 549/560; 568/665
[58] Field of Search .................... 528/365, 406, 407; 549/560, 523; 568/665

[56] References Cited

U.S. PATENT DOCUMENTS

| 3,226,214 | 12/1965 | Daniels et al. | 51/298 |
| 3,247,283 | 4/1966 | McGary et al. | 528/103 X |
| 3,404,102 | 10/1968 | Starcher et al. | 528/418 X |

Primary Examiner—Earl Nielsen
Attorney, Agent, or Firm—Ernest G. Szoke; John Daniel Wood

[57] ABSTRACT

Polyglycidyl ethers of tricyclodecane are provided which are useful as monomers in the production of cured epoxy resins. Also provided are polyallyl ethers of tricyclodecane which are novel intermediates in the preparation of the polyglycidyl ethers and a method of preparing the polyglycidyl ethers of this invention which uses the novel intermediates.

24 Claims, No Drawings

POLYGLYCIDYL ETHERS OF TRICYCLODECANE AND CURED EPOXY RESINS THEREFROM

BACKGROUND OF THE INVENTION

1. Field of the Invention

This invention relates to compositions containing polyglycidyl ethers of tricyclodecane that are useful as epoxy monomers in cured epoxy resins.

2. Description of Related Art

French Pat. No. 1,550,142 and German Pat. No. 1,645,222 disclose that dicyclopentadiene can be treated with carbon monoxide and hydrogen in the presence of cobalt to form diformyl-tricyclodecanes which can be hydrogenated to form di(hydroxymethyl)-tricyclodecanes which can in turn be treated with epichlorohydrin to form di(glycidyloxymethyl)ethers of tricyclodecane that are useful as epoxy monomers with diacid anhydrides or polyamines.

U.S. Pat. No. 3,404,102 discloses that a variety of di-, tri- and tetra-epoxy compounds which contain a bicyclo[2.2.1]heptyl ring, or larger fused homocarbocyclic ring of which the above heptyl ring system is an integral part, are useful as epoxy monomers in epoxy resins which in turn are useful as clear coatings and laminations. Several glycidyl ethers of tricyclo[5.2.1.0$^{2,6}$]decane are disclosed, including 3,4,8,10-tetrakis(2,3-epoxypropoxy)tricyclo(5.2.1.0$^{2,6}$)decane and 4,8-bis(2,3-epoxypropoxy)-tricyclo[5.2.1.0$^{2,6}$]decane.

SUMMARY OF THE INVENTION

This invention relates to compositions containing polyglycidyloxy epoxy compounds having the structural formula:

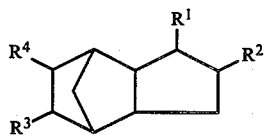

wherein $R^1$, $R^2$, $R^3$ and $R^4$ are selected from the group consisting of hydrogen, hydroxyl and glycidyloxy radicals, provided that at least three of $R^1$, $R^2$, $R^3$ and $R^4$ are glycidyloxy radicals. As used herein, the term "glycidyloxy" refers to an organic radical having the structural formula:

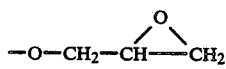

It has been found that the epoxy functionality of the compositions, as well as the structure of the epoxy compounds, also affects the performance of the composition in amino-cured epoxy resins. The preferred compositions have an epoxy functionality of greater than about 2, more preferably 2.4 or greater and most preferably 2.7 or greater.

This invention also relates to novel intermediates in the preparation of the polyglycidyl ethers of this invention and the use of these novel intermediates in preparing the polyglycidyl ethers of this invention. These novel intermediates are compositions containing polyallyl ethers of tricyclodecane which have the structural formula:

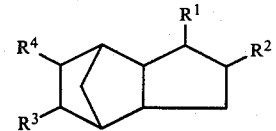

wherein $R^1$, $R^2$, $R^3$ and $R^4$ are selected from the group consisting of hydrogen, hydroxyl and allyloxy radicals provided that at least three of $R^1$, $R^2$, $R^3$ and $R^4$ are allyloxy radicals. As used herein, the term "allyloxy" refers to an organic radical having the structural formula:

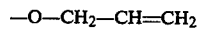

This invention further relates to amino-cured resins of the polyglycidyl ethers of this invention prepared by reacting the polyglycidyl ether containing compositions with an amino-containing compound. The amino-cured epoxy resins of this invention have outstanding properties, e.g. surprisingly high heat deflection temperatures.

DETAILED DESCRIPTION OF THE INVENTION

The compositions of this invention contain polyglycidyloxy substituted tricyclodecane compounds having the above structural formula wherein at least three of $R^1$, $R^2$, $R^3$ and $R^4$ are glycidyloxy radicals. Particularly preferred compounds are those wherein $R^1$ and $R^2$ are glycidyloxy radicals and (a) one of $R^3$ and $R^4$ is a glycidyloxy radical and the other is hydrogen or (b) both of $R^3$ and $R^4$ are a glycidyloxy radical. The compositions of this invention may be prepared by etherifying a tricyclodecane triol or tetrol of the appropriate structure with an epihalohydrin or by epoxidizing the polyallyl ether containing compositions of this invention.

Because the polyetherification reaction generally proceeds with less than 100% efficiency, the normal laboratory work-up of the reaction product will yield a mixture of compounds, i.e. primarily fully etherified product, and minor amounts of partially etherified products, by-products, and starting materials. This mixture is useful for the purposes contemplated herein and will yield cured epoxy resins having outstanding properties so long as the oxirane functionality of the epoxy mixture, calculated from the observed oxirane oxygen content of the mixture, is greater than about 2, preferably about 2.4 or greater, and most preferably about 2.7 or greater.

The polyglycidyl ethers of this invention are ultimately derived from dicyclopentadiene(3,8-tricyclo[5.2.1.0$^{2,6}$]decadiene) which has the structural formula:

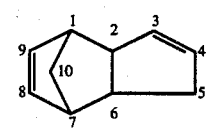

wherein the carbon atoms have been numbered according to the basic numbering system customarily used for dicyclopentadiene and dicyclopentadiene derivatives. The polyglycidyl ether compositions of this invention are prepared by hydroxylating or hydroxylating and hydrating the dicyclopentadiene to form a tetrol or any one of various triols of tricyclodecane wherein hydroxyl groups are bonded to any three or all four of the 3, 4, 8 and 9 carbons of tricyclodecane. These triols and the tetrol can then be polyetherified to form the polyglycidyl ethers of this invention.

The tricyclodecane triols and tetrol noted above are known compounds which may be synthesized by the hydroxylation and/or hydration of dicyclopentadiene. For example, U.S. Pat. No. 2,769,843 discloses that tricyclo[5.2.1.0$^{2,6}$]-decane-3,4,8(3,4,9)-triol can be prepared by the hydration of dicyclopentadiene to form a 8(9)-tricyclodecene-3-ol which can in turn be hydroxylated to form the triol by treatment with hydroxylating agents. Typical hydroxylating reactions include the treatment of an alkene with hydrogen peroxide and formic acid to form the formate polyester which can be hydrolyzed to the free polyol. Dicyclopentadiene can be directly hydroxylated in a similar manner to produce the tetrol as disclosed in British Pat. No. 799,753.

The polyglycidyl ethers of this invention are prepared from the tetrol and triols described above by one of two alternative synthetic routes. The tetrol or triols may be reacted with an epihalohydrin using phase transfer catalysis to form the polyglycidyl ethers in one step. In the alternative, the tetrol or triols may be reacted with an allyl halide in the presence of at least a stoichiometric amount of a strong base and a phase transfer catalyst to form the polyallyl ethers of this invention which are in turn epoxidized in a second step to form the polyglycidyl ethers. The latter method is preferred because the hydroxyl groups of the tetrol and triols can react with the epoxy moiety of the epihalohydrin to form by-product halohydrin ethers of tricyclodecane. These halohydrin ethers can in turn react with epihalohydrin to form halogenated ethers wherein the halogen atoms remain in the final product as aliphatic halogen. This residual halogen content is detrimental in epoxy resins in many applications, e.g. electronic components. Accordingly, the total halide content of the compositions is preferably minimized to less than 2%, more preferably less than 1% and most preferably less than 0.5%.

The etherification of the tricyclodecane triol or tetrol is generally accomplished by reacting the triol or tetrol with an epihalohydrin or an allyl halide and a strong base utilizing phase transfer catalysis. The preparation of the polyglycidyl ethers from the starting triols and tetrols employs the use of greater than stoichiometric amounts of the epihalohydrin or allyl halide. Suitable epihalohydrins or allyl halides include epichlorohydrin and epibromohydrin or allyl chloride and allyl bromide. Most conveniently, the epihalohydrin is epichlorohydrin or the allyl halide is allyl chloride.

General descriptions of the phase transfer catalysis technology are found in the text "Phase Transfer Catalysis Principles and Techniques," Starks and Liotta, Academic Press, New York 1978; and in "Phase Transfer Catalysis in Organic Synthesis", Weber and Gokel, Springer-Verlag. The phase transfer catalyst is any one of a numerous group of materials described in the aforementioned texts or in U.S. Pat. No. 3,992,432 to Napier, et al., the disclosure of which is herein incorporated by reference. Examples of suitable catalysts include tetrahexyl ammonium chloride, benzyl triethylammonium chloride, and tetrabutyl ammonium chloride.

When conducting the phase transfer reaction, it is preferable to prepare a premix which contains the starting triol or tetrol, the epihalohydrin or allyl halide, and the phase transfer catalyst in an organic solvent which is immiscible with aqueous caustic. Suitable organic solvents include aliphatic or aromatic hydrocarbons, e.g. toluene and t-amyl alcohol.

This premix is then mixed with a caustic aqueous solution of a strong base. A preferred strong base is sodium hydroxide. The concentration of the strong base in the aqueous solution generally ranges from about 20% to about 60% by weight, and most conveniently from about 45% to about 55%.

The two-phase mixture resulting from the addition of the premix to the basic aqueous solution is stirred for a time and at a temperature that will allow the reaction to proceed to substantial completion. Generally, reaction times vary from about 5 hours to about 24 hours, and reaction temperatures generally vary from about 10° C. to about 80° C. Preferred reaction temperatures are from about 25° C. to about 45° C.

The polyallyl ethers resulting from the use of an allyl halide in the above procedure are unsaturated compounds which may be epoxidized to form the polyglycidyl ethers of this invention by a variety of known methods. For example, the polyallyl ethers of this invention can be treated with an epoxidizing agent to produce the polyglycidyl ethers of this invention. Suitable epoxidizing agents include percarboxylic acids, hydroperoxides, and tungstic acid. Specific examples are peracetic acid and meta-chloroperbenzoic acid.

The polyglycidyl ethers of tricyclodecane of this invention are useful as monomers in cured epoxy resins, i.e. as epoxides cured with epoxy curing agents. An epoxy curing agent is any compound or composition that (a) will catalyze the homopolymerization of the polyglycidyl compounds of this invention to form an epoxy resin and/or (b) contains one or more functional groups that will react with the epoxy groups of the polyglycidyl compounds of this invention to form an epoxy resin. Examples of catalytic curing agents include Lewis acids and bases such as boron trifluoride and tertiary aliphatic amines such as triethylamine.

Representative epoxy curing agents having reactive functional groups include polycarboxylic acids, polycarboxy esters, polycarboxylic acid anhydrides, polyols, amines, polyamides, polythiols, polyisocyanates, polyisothiocyanates and the like.

The preferred epoxy curing agents are amino-containing compounds and polycarboxylic acid anhydrides. A specific example of a preferred polycarboxylic acid anhydride is a methylbicyclo[2.2.1]heptene-2,3-dicarboxylic anhydride.

The amino-containing compounds useful in curing the polyglycidyl compounds of this invention to form the epoxy resins of this invention are organic compounds which contain molecules in which at least two active hydrogen atoms are bonded to one or more nitrogen atoms. These compounds can be generally characterized as amines and polyamides.

As suitable amines, there may be mentioned aliphatic, cycloaliphatic or aromatic primary and secondary amines, with the aliphatic and cycloaliphatic amines being preferred. Typical amines include monoethanolamine, ethylenediamine, hexamethylenediamine, trimethylhexamethylenediamine, diethylenetriamine, triethylenetetramine, tetraethylenepentamine, N,N-dimethyl-1,3-propylenediamine, N,N-diethyl-1,3-propylenediamine, bis(4-amino-3-methylcyclohexyl)methane, bis(p-aminocyclohexyl)methane, 2,2-bis(4-aminocyclohexyl)- propane, N-aminoethyl-piperazine, m-phenylenediamine, p-phenylenediamine, bis(p-aminophenyl)methane, bis(p-aminophenyl)sulfone, m-xylylenediamine, 1,2-diaminocyclohexane, 1,4-diaminocyclohexane, 1,3-bis(aminomethyl)cyclohexane, 1,4-bis(aminomethyl)cyclohexane and isophorone diamine.

Preferred polyamides which are useful in the present compositions are those derived from polymeric fatty acids and aliphatic polyamines. Typically, these polyamides are those made from polymeric fatty acids containing up to about 22 carbon atoms in a monomeric acid with ethylene diamine and/or diethylene triamine. It will be appreciated that polyamide resins having terminal amine groups are preferred.

The polymeric fatty acids employed in preparing the polyamides are those resulting from the polymerization of drying or semi-drying oils, or the free acids or simply aliphatic alcohol esters of such acids. Suitable drying or semi-drying oils include soybean, linseed, tung, perilla, oiticica, cottonseed, corn, tall, sunflower, safflower, dehydrated castor oil, and the like. In the polymerization process for the preparation of the polymeric fatty acids, the fatty acids with sufficient double bond functionality combine for the most part, probably by a Diels Alder mechanism, to provide a mixture of dibasic and higher polymeric acids. The acids with insufficient functionality to react remain as monomers and may be wholly or partially removed, for example by distillation. The residue after distillation consists of the desired polymeric acids and this mixture is used for the preparation of the polyamide resin. In place of this method of polymerization, any other method of polymerization may be employed whether the resultant polymer possesses residual unsaturation or not. The term "polymeric fatty acids" as used herein, is intended to include the polymerized mixture of acids obtained, which mixture usually contains a predominant portion of dimeric acids, a smaller quantity of trimeric and higher polymeric acids, and some residual monomer.

These polymeric fatty acids may be reacted with a variety of aliphatic polyamines for the production of the polyamide. The amidification reaction may be carried out under the usual conditions employed for this purpose, as will be evident from the examples. Polyamides of this type generally have molecular weights varying from 1,000 to 10,000 and are resistant to the corrosive action of water, alkali, acids, oils, greases, and organic solvents. The melting points vary, depending upon the reactants and the reaction conditions. Where aliphatic diamines, such as ethylene diamine, are employed for the preparation of the polyamide the resin may melt within the approximate range of 100°-120° C., and usually within the range of 100°-105° C.

Higher melting polyamide resins, for example melting within the range of 130°-215° C., may be made by employing a mixture of polymeric fatty acids and other polybasic acids, the latter having at least two carboxyl groups which are separated by at least 3 and not more than 8 carbon atoms. Typical of these polybasic acids are the aliphatic acids, glutaric, adipic, pimelic, suberic, azelaic, and sebacic, and the aromatic acids, terephthalic, and isophthalic acids. The melting point of the copolymer resin may vary within the range previously indicated, depending upon the particular reactants, relative ratios thereof, as well as the reaction conditions.

Low melting polyamide resins melting within the approximate range of 25°-90° C. may be prepared from polymeric fatty acids and aliphatic polyamines having at least 3 atoms intervening between the amine groups principally involved in the amidification reaction. These three atoms may be carbon atoms or hetero atoms. Typical of the polyamines which may be used are diethylene triamine, triethylene tetramine, tetraethylene pentamine, 1,4-diaminobutane, 1,3-diaminobutane, hexamethylene diamine, 3-(N-isopropylamino)-propylamine, 3,3'-imino-bispropylamine, and the like. A preferred group of these low melting polyamides are derived from polymeric fatty acids, and diethylene triamine and are liquid at room temperature.

Suitable such polyamides are commercially available under the trade designation of VERSAMID® Polyamide resins. These are resins having a molecular weight ranging from about 3,000 to about 10,000, a softening point from below about room temperature to 190° C. and are prepared by condensing polymerized unsaturated fatty acids (e.g., dilinoleic acid) with aliphatic polyamines such as diethylene triamine.

The preparation of such VERSAMID® polyamide resins is well-known and by varying the acid and/or the functionality of the polyamine, a great variety of viscosities, molecular weights and levels of active amino groups spaced along the resin molecule can be obtained. Typically, the VERSAMID® polyamide resin have amine values from about 50 to 400; Gardner color (max.) of 8-10; and viscosities of from about 1 to 30 poises.

The preferred amino-containing compounds are polyamines having the general structural formula:

$$NH_2-R-(-NH-R-)_n-NH_2$$

wherein R is an alkylene, cycloalkylene, or arylene radical of up to about 8 carbon atoms and n is an integer having a value of from 0 to about 10. Particularly preferred compounds are those wherein R is an alkylene radical having from 2 to 4 carbon atoms and n is from 1 to 3. Most particularly preferred is triethylenetetramine wherein R is ethylene and n is 2.

The epoxy resins of this invention are obtained by mixing the polyglycidyloxy compound containing compositions with the amino-containing compound and curing the resulting mixture.

The amount of polyamine or polyamide employed in relation to the amount of polyglycidyloxy compound will vary somewhat, but will be a curing amount. In general, the amount of polyamine will be that amount required to furnish one amino hydrogen per epoxy group (stoichiometric amount), although up to about 50% excess of polyepoxide may be employed and up to about 100% excess of polyamine or polyamide may be employed.

It has been found that a representative polyglycidyloxy compound containing composition of this invention and the polyamine triethylenetetramine will gel at ambient temperatures in the absence of a catalyst about 30 to 35 minutes after mixing. Some of the polyglycidyloxy compound containing compositions of this invention may gel more slowly with polyamines and polyamides such that the application of heat may be desireable to shorten the gel time.

After mixing, the mixture can be used to form amino-cured epoxy resin products. For example, the mixture can be cured in a mold and subjected to a post-bake to obtain a useful cast article. A polyamine cured resin of a representative triglycidyl ether composition of this invention has been found to have outstanding physical properties. As shown in Example III, cured cast specimens of the triglycidyl ether of tricyclodecane, when cured with a representative polyamine and post-baked for 4 hours at 100° C., exhibited a heat deflection temperature, as measured by ASTM D 648-56, of 155° C. In contrast, when a diglycidyl ether of tricyclodecane, i.e. 3(4), 8(9)-bis(2,3-epoxypropoxymethyl)tricyclo[5.2.1.0$^{2,6}$]decane, is cured with triethylenetetramine under similar conditions, the heat deflection temperature of the cast specimens is only 71° C.

The high heat deflection temperature of the triethylenetetramine cured triglycidyltricyclodecane resins is comparable to that of commercial triethylenetetramine cure Novolac resins, e.g. Novolac resin DEN 438, available from Dow Chemical Co. However, those resins require post-bake temperatures of 160° C. to 200° C. to achieve the high heat deflection temperatures achieved by resins from the triglycidyltricyclodecanes of this invention.

EXAMPLE I

Preparation and Use of Triallyl Ether Intermediate to Prepare Triglycidyl-Tricyclodecane

Step 1

A 250 ml 3-necked round bottom flask equipped with condenser, addition funnel and a source of nitrogen gas was placed on a magnetic stirrer with a heating mantle. A premix solution consisting of triols, solvent, catalyst, and allyl chloride was prepared in the following manner. An amount, 60 g, of triol, a mixture of approximately equal amounts of 3,4,8-tricyclodecanetriol and 3,4,9-tricyclodecanetriol was weighed into and Erlenmeyer flask together with an equal portion of toluene. The catalyst, tetrabutyl ammonium chloride (6.7 g), and allyl chloride (15.8 g) were then added. The entire premix was stirred until a clear homogeneous solution was obtained. A 50% aqueous sodium hydroxide solution (31.5 ml) was charged into the round bottom and heated to 60° C. under a blanket of nitrogen gas. While vigorously stirring the caustic layer, the premix was dropwise added over a 15 minute period. The reaction was stirred at 60° C. for 4 hours.

The work-up procedure was begun by cooling the reaction to room temperature and diluting with an equal volume portion of water. After the phases separated, the organic layer was water washed again. Carbon dioxide gas was used to adjust the pH to 7. After the phases separated, the solvent was removed from the organic layer. The final product was filtered thru a pressure filter using a 0.1 micron pad.

Analysis of the product was done by gas chromatography/mass spectroscopy (GC/MS) and NMR. GC/MS of the major peak reported a m/e of 304 indicating the triallylated product and a m/e of 264 which indicates a diallyl ether/mono hydroxy isomer. NMR(CDCl$_3$): multiplet at 1.2–2.4 sigma(ring protons); multiplet at 3.1–4.2 sigma(—OCH$_2$); multiplet at 4.9–6.2 sigma(—CH=CH$_2$).

Step 2

A three-necked round bottom flask equipped with condenser and stirring bar was placed on a magnetic stirrer with a heating mantle. Meta-chloroperbenzoic acid (42 g) and solid sodium bicarbonate (16 g) were dissolved in 250 mls of methylene chloride and added to the flask. The solution was heated to reflux and 15 g of the allyl ether product of Step 1 was slowly added with stirring. The reaction was refluxed overnight.

Work-up procedure was begun by cooling the reaction to room temperature and washing with a 20% aqueous sodium bisulfite solution. The phases were separated and the organic was washed with three 100 ml portions of 10% sodium bicarbonate. After separation, the organic layer was water washed with three 100 ml portions. The organic layer was stripped of solvent and filtered through a 0.1 micron pad.

The final product was analyzed by oxirane titration, and total chloride. The oxirane oxygen content was 12.5% indicating oxirane functionality of 2.76 (a composite with the theoretical oxirane functionality of 3 would contain 13.6% oxirane oxygen). The total chloride was 0.44%.

EXAMPLE II

Use of Epichlorohydrin to Prepare Triglycidyl-Tricyclodecane

A 250 ml three-necked round bottom flask equipped with condenser, addition funnel and nitrogen source was placed on a magnetic stirrer with a heating mantle. A premix solution consisting of 18 g of the alcohol, solvent (t-amyl alcohol 40 g), catalyst, tetrabutyl ammonium chloride (2.2 g) and epichlorohydrin (70 g) were combined and warmed to 40° C. A 50% aqueous sodium hydroxide solution (63 ml) was charged into the round bottom flask and heated to 40° C. While vigorously stirring the alkaline portion, the premix was dropwise added over a 40 minute period. The reaction continued for an additional 4 hours at 40° to 50° C.

Work-up was begun by cooling the reaction and separating the phases. The organic layer was washed twice. Carbon dioxide was bubbled moderately through the entire mixture for approximately 10 minutes until a pH of 7 was reached. After phase separation, the organic layer was stripped of solvent. The final product was filtered through a 0.1 micron pad.

The product was analyzed by GC, GC/MS, oxirane, total chloride, Gardner color and viscosity. GC/MS showed a major peak with a M/e of 352. The oxirane oxygen content was 7.8% which indicates a theoretical functionality of 1.7. The total chloride was 2.24%, Gardner color was 13 and the viscosity was 9.4 ps. The GC of the sample indicated only 33% of the product mixture was the desired triglycidyl ether.

This example demonstrates that the epichlorohydrin route to the compositions of this invention is generally inferior to the allyl halide route. The oxirane functionality of the above product could have been increased with the use of greater amounts of epichlorohydrin, which in turn should increase the chloride content of the product.

EXAMPLE III

Triethylenetetramine Cured Triglycidyl-Tricyclodecane

An amount, 127.9 parts by weight, of tricyclodecane triglycidyl ether was mixed with with 24.33 parts of triethylene tetramine. This weight ratio results in a 1 to 1 ratio of amine hydrogen to epoxide oxirane. After initial mixing, this mixture was allowed to sit for 5 minutes. The mixture was then mixed a second time to ensure its homogeneity.

The resin blend was then poured into a mold. The liquid mixture was allowed to gel in the mold and then continue to cure for 16 hours at ambient temperatures. The solidified plastic was demolded and post-cured for 4 hours at 110° C.

The post-cured plastic was then cut into a bar, ⅛" by ½" by 4", and tested for heat distortion temperature according to ASTM D 648-56. The heat distortion temperature of the test specimen was found to be 155° C.

Another test specimen cured the same way as described above. The specimen was cut as described in ASTM D 638-60 for tensile and elongation testing. The tensile strength and ultimate elongation of the test specimen was found to be 7,571 psi and 4%, respectively.

EXAMPLE IV

Nadic Methyl Anhydride Cured Triglycidyl Tricyclodecane

An amount, 100 grams, of tricyclodecane triglycidyl ether (average functionality of 2.5) was mixed with 108.40 grams of anhydride curing agent Nadic Methyl Anhydride (isomers of methylbicyclo[2.2.1]heptene-2,3-dicarboxylic anhydride) obtained from Buffalo Color. To this mixture was added 1.5 grams of amine catalyst benzyldimethylamine. This mixture appeared clear and compatable. The mixture was poured into a mold. The mold was heated for two hours at 90° C. Gellation of the mixture occurred between the initial application of heat and 1.25 hours. After the two hour bake at 90° C., the mold and the gelled plastic was post-baked at 165° C. for four hours. The post-cured plastic was allowed to cool to ambient temperature and was demolded. The plastic was then post-cured a second time at 200° C. for sixteen hours and allowed to cool to ambient temperatures. The 200° C. post-cured plastic was then cut into a bar ⅛" by ½" by 4" and tested for heat distortion temperature according to ASTM D-648-56. The heat distortion temperature of the test specimen was found to be 187° C.

By comparison, Dow Chemical Company's epoxy Novolac resin DEN 431 (average functionality of 2.2) and DEN 438 (average functionality of 3.6), which are poly(glycidyloxyphenyl-methylene) resins, when cured with nadic methyl anhydride have heat distortion temperatures of 162° C. and 183° C. These values were taken from a Dow Chemical Company literature booklet entitled "Dow Epoxy Novolac Resins", form No. 190-279-78.

What is claimed is:

1. A composition of matter comprising a polyglycidyloxy compound having the structural formula:

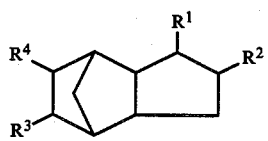

wherein $R^1$, $R^2$, $R^3$ and $R^4$ are selected from the group consisting of hydrogen, hydroxyl and glycidyloxy radicals, provided that at least three of $R^1$, $R^2$, $R^3$ and $R^4$ are glycidyloxy radicals.

2. A composition in accordance with claim 1 having an epoxy functionality of greater than about 2.

3. A composition in accordance with claim 1 having a halide content of less than about 2% by weight.

4. A composition in accordance with claim 1 comprising a compound wherein $R^1$ and $R^2$ are glycidyloxy radicals and one of $R^3$ and $R^4$ is a glycidyloxy radical and the other is hydrogen.

5. A composition in accordance with claim 1 comprising a compound wherein $R^1$, $R^2$, $R^3$ and $R^4$ are glycidyloxy radicals.

6. A method of preparing a polyglycidyloxy compound containing composition in accordance with claim 1 comprised of:

(a) reacting an allyl halide with a compound having the formula:

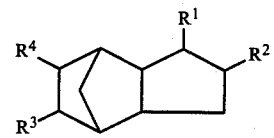

wherein $R^1$, $R^2$, $R^3$ and $R^4$ are hydrogen or hydroxyl, provided that at least three of $R^1$, $R^2$, $R^3$ and $R^4$ are hydroxyl; in the presence of at least a stoichiometric amount of a strong base and a phase transfer catalyst; and (b) reacting the allyl ether product from step (a) above with an epoxidizing agent.

7. A method in accordance with claim 6 wherein $R^1$ and $R^2$ are hydroxyl groups and one of $R^3$ and $R^4$ is a hydroxyl group and the other is hydrogen.

8. A method in accordance with claim 6 wherein $R^1$, $R^2$, $R^3$ and $R^4$ are hydroxyl groups.

9. A composition of matter comprising a polyallyloxy compound having the structural formula:

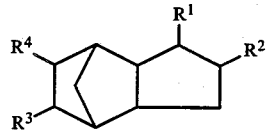

wherein $R^1$, $R^2$, $R^3$ and $R^4$ are selected from the group of hydrogen, hydroxyl and allyloxy radicals provided that at least three of $R^1$, $R^2$, $R^3$ and $R^4$ are allyloxy radicals.

10. A composition in accordance with claim 9 comprising a compound wherein $R^1$ and $R^2$ are allyloxy radicals and one of $R^3$ and $R^4$ are allyloxy radicals and the other is hydrogen.

11. A composition in accordance with claim 9 comprising a compound wherein $R^1$, $R^2$, $R^3$ and $R^4$ are allyloxy radicals.

12. An epoxy resin formed by reacting a polyglycidyloxy containing composition in accordance with claim 1 with an epoxy curing agent.

13. An epoxy resin in accordance with claim 12 wherein the polyglycidyloxy compound containing composition has an epoxy functionality greater than about 2.

14. An epoxy resin in accordance with claim 12 wherein the polyglycidyloxy containing composition has a halide content of less than about 2%.

15. An epoxy resin in accordance with claim 12 comprising a compound wherein $R^1$ and $R^2$ are glycidyloxy radicals and one of $R^3$ and $R^4$ is a glycidyloxy radical and the other is hydrogen.

16. An epoxy resin in accordance with claim 15 wherein the epoxy curing agent is a polyamine having the structural formula:

wherein R is an alkylene, cycloalkylene, or arylene radical of up to about 8 carbon atoms and n is an integer having a value from 0 to about 10.

17. An epoxy resin in accordance with claim 16 wherein R is an alkylene radical having from 2 to 4 carbon atoms and n is from 1 to 3.

18. An epoxy resin in accordance with claim 17 wherein R is ethylene and n is 2.

19. An epoxy resin in accordance with claim 12 comprising a compound wherein $R^1$, $R^2$, $R^3$ and $R^4$ are glycidyloxy radicals.

20. An epoxy resin in accordance with claim 19 wherein the epoxy curing agent is a polyamine having the structural formula:

wherein R is an alkylene, cycloalkylene, or arylene radical of up to about 8 carbon atoms and n is an integer having a value from 0 to about 10.

21. An epoxy resin in accordance with claim 20 wherein R is an alkylene radical having from 2 to 4 carbon atoms and n is from 1 to 3.

22. An epoxy resin in accordance with claim 21 wherein R is ethylene and n is 2.

23. An epoxy resin in accordance with claim 12 wherein the epoxy curing agent is a polycarboxylic acid anhydride.

24. An epoxy resin in accordance with claim 23 wherein the epoxy curing agent is a methylbicyclo[2.2.1]heptene-2,3-dicarboxylic anhydride.

* * * * *